United States Patent
Ahmed et al.

(10) Patent No.: US 7,532,325 B2
(45) Date of Patent: May 12, 2009

(54) METHOD AND APPARATUS FOR THE SEPARATION OF FLUOROSCENCE AND ELASTIC SCATTERING PRODUCED BY BROADBAND ILLUMINATION USING POLARIZATION DISCRIMINATION TECHNIQUES

(75) Inventors: Samir A. Ahmed, New York, NY (US); Fereidun Moshary, New York, NY (US); Barry Michael Gross, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 295 days.

(21) Appl. No.: 10/573,056

(22) PCT Filed: Sep. 23, 2004

(86) PCT No.: PCT/US2004/031487

§ 371 (c)(1), (2), (4) Date: Jan. 19, 2007

(87) PCT Pub. No.: WO2005/028062

PCT Pub. Date: Mar. 31, 2005

(65) Prior Publication Data

US 2007/0171410 A1    Jul. 26, 2007

(51) Int. Cl.
G01J 3/447 (2006.01)
G01J 3/30 (2006.01)

(52) U.S. Cl. ............. 356/327; 356/317; 356/322; 356/72; 356/364

(58) Field of Classification Search ............ 356/317, 356/318, 322–327, 72, 73, 364–369
See application file for complete search history.

(56) References Cited

U.S. PATENT DOCUMENTS 6,624,890 B2    9/2003    Backman et al.
2004/0249274 A1    12/2004    Yaroslavsky et al.

OTHER PUBLICATIONS

Fuchs, "Separating the Fluorescence and Reflectance Components of Coral Spectra," Applied Optics, vol. 40, No. 21, pp. 3614-3621 (Jul. 20, 2001).
Cunningham, et al., "Brewster-angle Measurements of Sea-surface Reflectance Using a High Resolution Spectroradiometer," J. Opt. A: Pure Appl. Opt. 4, S29-S33 (2002).

(Continued)

Primary Examiner—L. G Lauchman
(74) Attorney, Agent, or Firm—Hoffmann & Baron, LLP; Irving N. Feit

(57) ABSTRACT

An apparatus for separating fluorescent light from light elastically scattered/reflected from a material illuminated with a broadband illumination source includes a polarization discriminator, which separates the substantially polarized elastically scattered/reflected light from the unpolarized fluorescent light, and a spectrometer to analyze the full and separated reflectance spectra. A linear polarizer may be provided to polarize the illumination source. A method for separating fluorescence light induced in a material by broadband light from an elastic scattering/reflection component includes providing polarization discrimination to separate the components, the fluorescence light being substantially unpolarized, and spectrally analyzing the reflectance components. The method may include linearly polarizing the light source. A fluorescence spectra may be extracted from a minimum reflectance spectra or from a residual polarization reflectance spectra.

52 Claims, 8 Drawing Sheets

OTHER PUBLICATIONS

S.P. Schilders, et al., "Effect of Scatterer Size on Microscopic Imaging Through Turbid Media Based on Differential Polarisation-Gating," Optics Communications 157, pp. 238-248 (1998).

J.M. Schmitt, et al., "Use of Polarized Light to Discriminate Short-Path Photons in a Multiply Scattering Medium," Applied Optics, vol. 31, No. 30, pp. 6535-6546 (Oct. 20, 1992).

S.G. Demos, et al., "Temporal Gating in Highly Scattering Media by the Degree of Optical Polarization," Optics Letters, vol. 21, No. 2, pp. 161-163 (Jan. 15, 1996).

Stephen P. Morgan, et al., "Effects of Polarization State and Scatterer Concentration on Optical Imaging Through Scattering Media," Applied Optics, vol. 36, No. 7, pp. 1560-1565 (Mar. 1, 1997).

J.F.R. Gower, et al., "Interpretation of the 685 nm Peak in Water-Leaving Radiance Spectra in Terms of Fluorescence, Absorption and Scattering, and its Observation by MERIS," Int. J. Remote Sensing, vol. 20, No. 9, pp. 1771-1786 (1999).

A.A. Gitelson, et al., "Remote Estimation of Chlorophyll Concentration in Productive Waters: Principals, Algorithm Development and Validation," Proc. of NWQMC, 149 (2000).

METHOD AND APPARATUS FOR THE SEPARATION OF FLUOROSCENCE AND ELASTIC SCATTERING PRODUCED BY BROADBAND ILLUMINATION USING POLARIZATION DISCRIMINATION TECHNIQUES

FIELD OF THE INVENTION

The present invention relates generally to fluorescence measurements, and more particularly, to a method and apparatus for separating fluorescence from elastic reflection and scatter components in the reflectance spectra of an object illuminated with broadband light, using polarization discrimination techniques.

BACKGROUND OF THE INVENTION

The separation of fluorescence and elastic scatter/reflection components of fluorescing materials illuminated by white light (or sunlight) is of interest for a variety of environmental remote sensing, medical diagnostics, and colorimetry applications. These include the study of upwelling radiation from algae in sea water, where the magnitude of the fluorescence peak can be considered as a measure of chlorophyll concentration and photosynthetic activity, as described in A. A. Gitelson, et al., "Remote Estimation of Chlorophyll Concentration in Productive Waters: Principals, Algorithm Development and Validation," *Proc. of NWQMC*, 149 (2000). Applications also include the examination of coral reefs containing fluorescing pigments, as described in J. F. R. Gower, et al., "Interpretation of the 685 m Peak in Water-Leaving Radiance Spectra in Terms of Fluorescence, Absorption and Scattering, and its Observation by MERIS," *Int. J. Rem. Sens.*, No. 20, 1771 (1999).

A variety of techniques have been used to effect this separation in experimental measurements. Dual monochromator techniques utilize monochromatic sources and detectors which must be carefully and selectively tuned over appropriate spectral ranges to measure true elastic reflectance, as discussed in F. Grum, "Colorimetry of Fluorescent Materials," *Optical Radiation Measurements*, Vol. 2, Chap. 6 (Academic Press, New York, 1980). Other techniques use a series of bandpass filters to separate elastic and inelastic components. These methods are particularly effective where the fluorescence is characterized by large Stokes shifts, but involve a complicated multiple-step procedure.

A recent approach, which is described in E. Fuchs, "Separating the Fluorescence and Reflectance Components of Coral Spectra," *Appl. Opt.* No. 40, p. 3614 (2001), makes use of measurements with and without sharp long pass filters to permit in-situ measurements and separation of elastic reflectance and fluorescence from coral reefs.

There is a need, therefore, for a simple and accurate method and apparatus that provide the separation of fluorescence components from the elastic reflection components in the reflectance spectra of an illuminated object.

SUMMARY OF THE INVENTION

The present invention relates to a method for separating fluorescence light, induced in a material by a light source, from elastically scattered/reflected light in a full reflectance spectrum of the material. The method includes comparing the full reflectance spectrum to a residual polarization reflectance spectrum over a non-fluorescent portion of the spectrum of the light source. The residual polarization reflectance spectrum includes substantially no fluorescent light. The method also includes extrapolating a fluorescence spectrum, which represents a spectral dependence of the fluorescence light over the source spectrum, from the residual polarization reflectance spectrum and the full reflectance spectrum.

The act of comparing may further include measuring a maximum polarization reflectance spectrum, measuring a minimum polarization reflectance spectrum, and calculating the residual polarization reflectance spectrum as a difference between the maximum and the minimum polarization reflectance spectra.

The method may also include fitting the residual polarization reflectance spectrum into the full reflectance spectrum over the nonfluorescing portion of the spectrum to derive a fitted reflectance spectrum. The fitted reflectance spectrum represents substantially only the elastically scattered/reflected light over the source spectrum.

The present invention also relates to a method for separating fluorescent light induced in a material by a light source from elastically scattered/reflected light in a full reflectance spectrum of the material. The method includes providing a linearly polarized light source, measuring a minimum reflectance spectrum, and extracting a fluorescence spectrum from the minimum reflectance spectrum. The minimum reflectance spectrum includes a cross polarized component of the elastically scattered/reflected light.

The act of extracting may further include multiplying the minimum reflectance spectrum by a scale factor and correcting the scale of the minimum reflectance spectrum background.

The present invention also relates to a method for separating unpolarized light from backscattered/reflected light in a full reflectance spectrum of a surface illuminated by a light source having a spectrum. The method includes comparing the full reflectance spectrum to a residual polarization reflectance spectrum over a portion of the spectrum comprising substantially no unpolarized light. The residual polarization reflectance spectrum includes substantially no unpolarized light. The method also includes extrapolating an unpolarized spectrum of the unpolarized light over the spectrum from residual polarized reflectance spectrum and the full reflectance spectrum.

The light source of the method of the present invention may include a broadband spectrum. The broadband spectrum may additionally be provided by sunlight.

The present invention also relates to a method for separating thermal radiation from solar illumination wherein the unpolarized light includes thermal radiation and the polarized light represents backscattered/reflected solar illumination.

The method of the present invention may further be adapted for use with environmental remote sensing. The method may include calculating chlorophyll fluorescence and concentration of vegetation from the fluorescence spectrum, where the fluorescence light spectrum corresponds to the unpolarized light spectrum.

The method of the present invention may alternately be adapted for use in medical diagnostics, where the material illuminated by the light source includes a specimen, a living tissue, or other bodily material. This method further includes diagnosing a medical condition from the fluorescence spectrum.

The present invention additionally relates to an apparatus for separating unpolarized light induced in a material by a light source from elastically scattered and/or elastically reflected polarized light in a full reflectance spectrum of the material. The apparatus includes a detector, a spectrometer, and an analyzing polarizer. The spectrometer and detector are used to measure at least the full reflectance spectrum. The detector includes an axis of detection with a scattering angle being measured between a direction of the illuminating light and the axis of detection. The analyzing polarizer is used to measure at least one of a minimum detected polarization reflectance spectrum and a residual polarization reflectance spectrum, by adjusting the analyzing polarizer in front of the detector. The spectrum of the unpolarized light is extrapolated from the at least one of the minimum detected polarization reflectance spectrum and the residual polarization reflectance spectrum.

The apparatus of the present invention may be adapted for use in a Raman lidar system, where the elastically scattered/reflected polarized light includes Raman backscatter.

The apparatus of the present invention may also be adapted for use in an environmental remote sensor, which uses the spectrum of the fluorescent light, measured as the unpolarized light component according to the present invention, to calculate chlorophyll fluorescence of vegetation.

The apparatus of the present invention may alternately be adapted for use in a medical diagnostic system, which uses the fluorescent light spectrum as an indicator in diagnosing a medical condition.

The present invention also relates to an apparatus for separating fluorescent light induced in a material by a light source from elastically scattered and/or elastically reflected polarized light in full reflectance spectrum of the material. The light source includes a broadband illumination source. The apparatus includes a polarization discriminator, which separates the elastically scattered/reflected light from the fluorescent light. The fluorescent light is substantially unpolarized and the elastically scattered reflected light is substantially polarized. The apparatus also includes a spectrometer, which spectrally analyzes the fluorescent light and the elastically scattered/reflected light.

The apparatus may also include a linear polarizer for polarizing the illuminating source.

The present invention additionally relates to an apparatus for separating fluorescent light from light elastically scattered/reflected from a material illuminated with a broadband illumination source. The apparatus includes a polarization discriminator, which separates the substantially polarized elastically scattered/reflected light, from the substantially unpolarized fluorescent light. The apparatus further includes a spectrometer for spectrally analyzing the fluorescent light and the elastically scattered/reflected light.

The present invention further relates to a method for separating fluorescence light induced in a material by broadband light from an elastic scattering/reflection component of the broadband light. The method includes providing polarization discrimination to separate the substantially unpolarized fluorescence light from the at least partially polarized elastic scattering/reflection component, and spectrally analyzing the fluorescence light and the elastic scattering/reflection component.

The present invention still further relates to an apparatus for-separating between fluorescence light from a sample and light elastically scattered/reflected from the same sample illuminated with a broadband excitation illumination source. The apparatus makes use of the polarization properties of scattered light and the unpolarized nature of fluorescence to separate and distinguish the different components.

The apparatus may include a broadband source and polarizer for illumination of the sample medium with polarized light by passing the broadband illuminating light through the polarizer to illuminate the sample. The apparatus may also include a detector and polarization discriminator. Polarization discrimination is then performed, for example, by a polarization discriminator including a rotating polarizer, or a polarizing prism arrangement, in front of the detector to separate the polarized scattered light, which has retained some of its original polarization, from the unpolarized fluorescence. A method of polarization discrimination may include rotating the rotating polarizer in front of the detector for maximum and minimum values related to the polarization of the scattered signal. The detected light is then collected and analyzed in a spectrometer.

Another arrangement may illuminate the material sample with unpolarized light and make use of an analyzing polarizer in front of the detector to separate the unpolarized fluorescence from partially polarized scattering.

Yet another arrangement makes use of some natural polarization occurring in the illuminating light and an analyzing polarizer in front of the detector to separate the unpolarized fluorescence from partially polarized scattered light.

A method for separating fluorescence light induced in a sample by broad band light excitation from the elastic scattering/reflection of the broadband excitation light, substantially comprises polarizing the broadband excitation light illuminating the sample (with a polarizer) and then using a detector arrangement and geometry with a rotating polarizer or other polarization discrimination technique such as a polarizing prism in front of the detector to separate and evaluate the resulting polarized scattered/reflected broadband light and the unpolarized fluorescence from the sample and collect these and analyze them in a spectrometer.

In another embodiment of the method, the sample is illuminated by unpolarized light and then polarization discrimination is used in front of the detector, to separate the partially polarized light resulting from the scatter/reflection process to distinguish it from the unpolarized fluorescence.

Yet another embodiment comprises illumination of the sample by naturally polarized light such as sunlight, and using discrimination by a polarizer placed in front of the detector to discriminate and evaluate between the unpolarized fluorescence and the partially polarized elastically scattered/reflected sunlight from the sample.

BRIEF DESCRIPTION OF THE DRAWINGS

FIG. 8b is a plot of the total measured reflectance spectra and the extrapolated sun-induced fluorescence from the substance (algae) using the apparatus of FIG. 8a.

DETAILED DESCRIPTION OF THE INVENTION

Figure 1A:
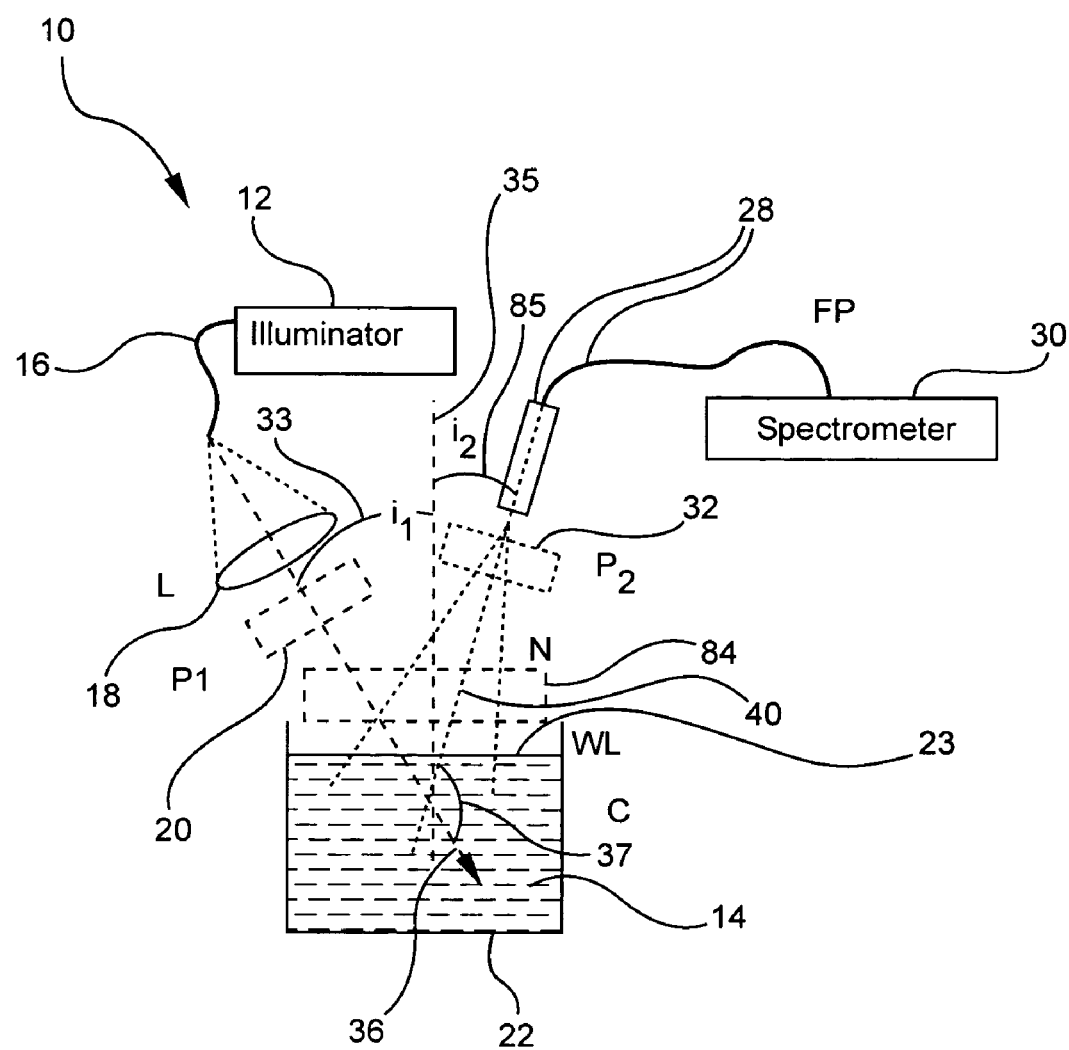
FIG. 1a is a schematic representation of an embodiment of an apparatus formed in accordance with the present invention for separating the elastic scatter/reflection components from the fluorescence component in the reflectance spectra of an illuminated material.

The device and method of the present invention are based upon the polarization properties of elastically scattered light and the unpolarized nature of excited fluorescence. The present invention provides the separation of the elastic scattering and fluorescence components in the reflectance spectra of an illuminated object.

The terms "spectrum" and "spectra" are used interchangeably herein to refer to a spectral dependence.

In the method of the present invention, a polarization discrimination technique is provided to separate elastic reflectance and fluorescence components resulting from white light illumination. The technique can be applied to any fluorescing materials illuminated by broadband sources, or even narrow band sources where the reflectance and fluorescence overlap.

A method for separating fluorescence light induced in a sample by broad band light excitation from the elastic scattering/reflection of the broadband excitation light comprises polarizing the broadband excitation light illuminating the sample (with a polarizer). A polarization discrimination technique is applied, e.g., an analyzing polarizer such as a rotating polarizer, polarizing prism, or other linear polarizer is used in front of a detector. The arrangement and geometry of the detector and analyzing polarizer permits separation and evaluation of the resulting polarized scattered/reflected broadband light and the unpolarized fluorescence from the sample, which are collected and analyzed in a spectrometer.

In another embodiment of the method, the sample is illuminated by unpolarized light and then polarization discrimination is used in front of the detector to separate the partially polarized light resulting from the scatter/reflection process from the unpolarized fluorescence.

Yet another embodiment comprises illumination of the sample by naturally polarized light such as sunlight, and using discrimination by a polarizer placed in front of the detector to discriminate and evaluate between the unpolarized fluorescence and the partially polarized elastically scattered/reflected sunlight from the sample.

The method and apparatus of the present invention may be applied to any material or material particles which fluoresce (e.g., algae) with broadband illumination. Material particles may include at least one of a sphere shape, an ellipsoidal shape, and a plate-like shape.

Preferably, the method and apparatus of the present invention include fluorescent material particles having a dimension equal to or greater than about 2 microns.

In another embodiment, the fluorescent material particles include a dimension less than or equal to about 20 microns.

An apparatus formed in accordance with the present invention for separating between fluorescence light from a sample and light elastically scattered/reflected from the same sample of a broadband excitation illumination source makes use of the polarization properties of scattered light and the unpolarized nature of fluorescence to separate and distinguish the different components. In one embodiment, the apparatus may include illuminating polarized light for illuminating the sample medium. The polarized illumination may be produced by passing the broadband illuminating light through a polarizer to illuminate the sample.

The apparatus also includes polarization discrimination elements, for example, a rotating polarizer, or a polarizing prism arrangement, in front of the detector to separate the polarized scattered light which has retained some of its original polarization from the unpolarized fluorescence. The rotating polarizer is rotated in front of the detector to obtain maximum and minimum values related to the polarization of the scattered signal. The detected light is then collected and analyzed in a spectrometer.

The polarization discrimination elements may include any polarization device known in the art capable of at least separating linear polarization components, e.g., perpendicular and parallel linear polarization components, in a detected light signal such as reflectance spectra. The polarization discrimination element in front of the detector of the present invention, also referred to as a polarizer or analyzing polarizer, may include any linearly polarizing device, including a rotatable linear polarizer or polarizing prism.

The detector of the present invention may include any detector known in the art capable of resolving the spectral dependence of the reflectance spectra of the polarized and unpolarized components over the spectrum of interest of the elastically scattered and fluorescent light.

The spectrometer of the present invention may include any device capable of spectrally analyzing, i.e., resolving, the reflectance spectra over the spectrum of the reflected/scattered and fluorescing light, including spectrally resolving a fluorescent peak.

Another embodiment of the apparatus of the present invention includes unpolarized illuminating light and a polarization discrimination element, e.g., a polarizer referred to herein as an analyzing polarizer, in the detector to separate the unpolarized fluorescence from partially polarized scattering.

Yet another embodiment makes use of some natural polarization occurring in the illuminating light and a polarizer in the detector to separate the unpolarized fluorescence from partially polarized scattered light.

FIG. 1a represents an embodiment 10 of the apparatus of the present invention for separating the elastic scatter/reflection components from the fluorescent components in the reflectance spectra of an illuminated material 14. Referring to FIG. 1a, an illuminating angle $i_1$ 33 is defined as the angle between the illuminating light 36 and the normal 35 to the surface of a material 14 being irradiated. A detection angle $i_2$ 85 is defined as the angle between the surface normal 35 and detector axis 40. A scattering angle $\theta$ 37 is the angle at which scattered light is detected and is defined as the angle between the detector axis 40 and the direction of illumination 36. As shown in FIG. 1a, the method and apparatus of the present invention may include any combination of illumination angle 33, detection angle 85 and scattering angle 37 for which detectable reflectance spectra may be obtained.

Referring again to FIG. 1a, the apparatus 10 of the present invention includes an analyzing polarizer P2 32, a fiber-probe collector (FP) 28, and a spectrometer 30. The apparatus 10 may also include a source polarizer.

In the embodiment 10 shown in FIG. 1a, a source of illumination for illuminating the material 14 is provided by an illuminator 12 coupled to a fiber optic light guide 16. The output from the fiber optic 16 is collimated by collimating lens L 18 before impinging on the sample material 14. A cuvette (C) 22 is provided to contain the material 14, for example, algae, in water. The water level (WL) 23 is also indicated in FIG. 1a.

The method and apparatus of the present invention have been applied to measurements on algae in sea water. Two types of algae were tested: *Isochrysis* and *Tetrasecinis striata*. While these experiments were carried out in the laboratory, with both artificial and sunlight sources, the simplicity of the technique makes it applicable to a variety of field conditions.

Figure 1B:
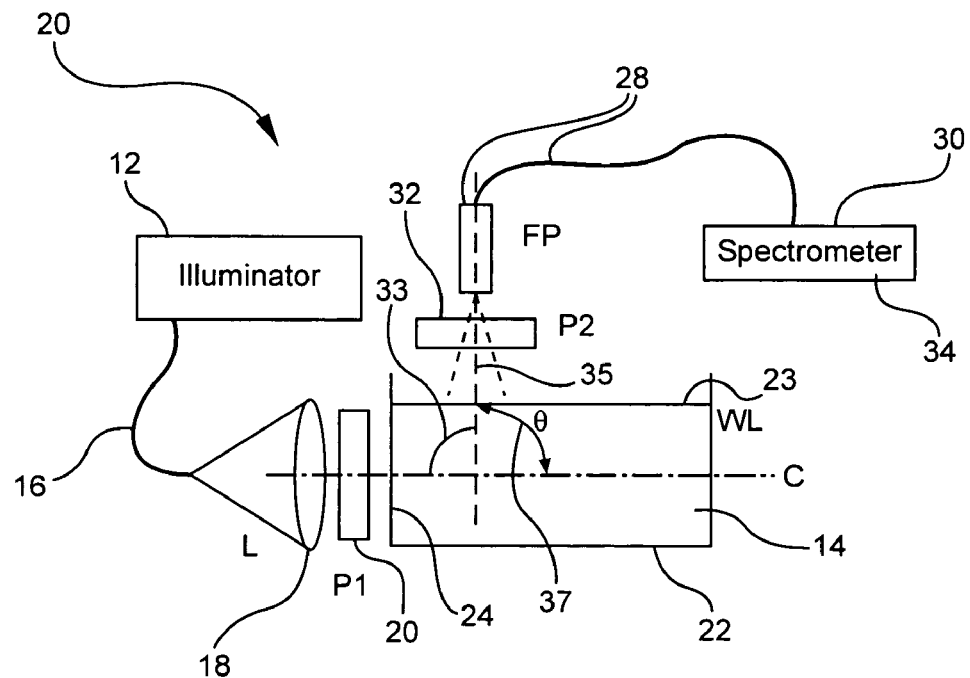
FIG. 1b is another embodiment of the apparatus of the present invention, which includes one polarizer to linearly polarize the light illuminating the material and one polarizer before the detector to analyze the polarization components.

The essential features of an embodiment of a method and apparatus 20 of the present invention are illustrated by the experimental set up shown in FIG. 1b. In this embodiment, horizontally polarized collimated white light from 150 W EKE lamp of PL-900 Dolan Jenner illuminator 12 is used to illuminate a sample 14, e.g., sea-water containing algae, through a fiber optic light guide 16, collimating lens 18 and polarizer P1 20. The material to be tested in our experiments was sea-water with the algae, which was placed in the cuvette C 22. One wall of the cuvette 22 was replaced by a microscopic slide 24 for illumination and all others were covered with the black tape to minimize reflection. The collection optics consisting of a fiber optic collector and probe 28 (multimode fiber with 200-μm core diameter) coupled to a SQ-2000 fiber optic spectrometer 30 (Ocean Optics) collected the elastically scattered/reflected and fluorescence light from the illuminated site with geometries such that the light was captured over a 24 degrees angle (fiber's numeric aperture is 0.22). The fiber probe 28 was installed vertically 30 mm above the surface of the water. A rotatable polarizer P2 32 was placed in front of the probe 28 and detector 34 (not shown, in the spectrometer 30). The directions of the incident light 36, scattered light 40 and polarization components representing the configuration of FIG. 1b are shown in FIG. 1c.

Referring to FIG. 1b, the illumination or incident angle 33 is the angle between the incident light 36 and the surface normal 35 of the material 14. The scattering angle 37 is the angle between the direction of illumination 36 at the material 14 and the direction or axis of detection 40. In this embodiment, both the incident angle 33 and the scattering angle are ninety degrees (90°).

Figure 1C:
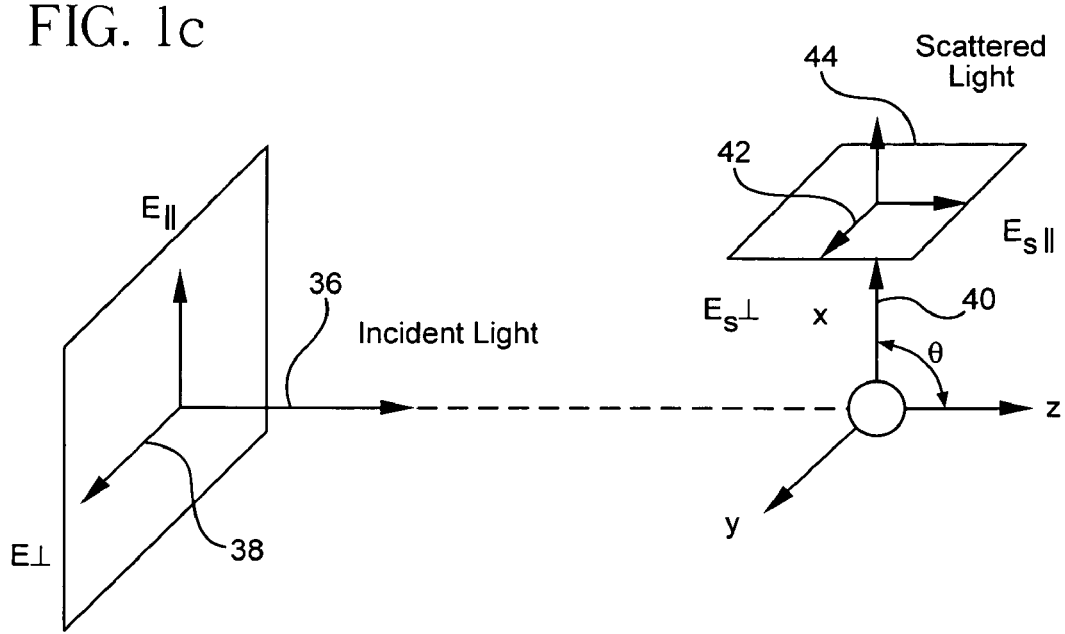
FIG. 1c is a vector representation of the polarization components of the scattered/reflected light.

Referring to FIG. 1c, in the initial approach, shown in FIG. 1b, the polarizer P1 20 is oriented to illuminate the sample 14 with horizontally polarized light 38, which is in fact perpendicular to the scattering plane formed by the incident illumination 36 and the axis of detection 40. This horizontally polarized illuminating light which is scattered vertically by the algae will largely retain its polarization (with respect to direction of propagation) after undergoing the elastic scatter/reflection process. This is the case for many types of scattering, including scattering by surfaces with radii large compared to the wavelength (such as the algae) as well as for scattering by dipoles. On the other hand, fluorescence produced by the illuminated algae will be unpolarized. This will reach the detector directly, or in the case of higher algae concentration, after forward scattering by algae or other particulates which would still leave it unpolarized (the illumination and detector geometry ensure that it is primarily direct fluorescence or the forward scattered fluorescence can reach the detector).

Rotation of the polarizer in front of the detector will therefore cause the detected elastic scatter component to vary from a maximum, $R_\perp(\lambda)$, (representing the vector component of the scattered light parallel to the retained original polarization 42), to essentially zero, for $R_\parallel(\lambda)$, the cross polarized component of the scattered light 44, while leaving the detected fluorescence signal unchanged.

Figure 2:
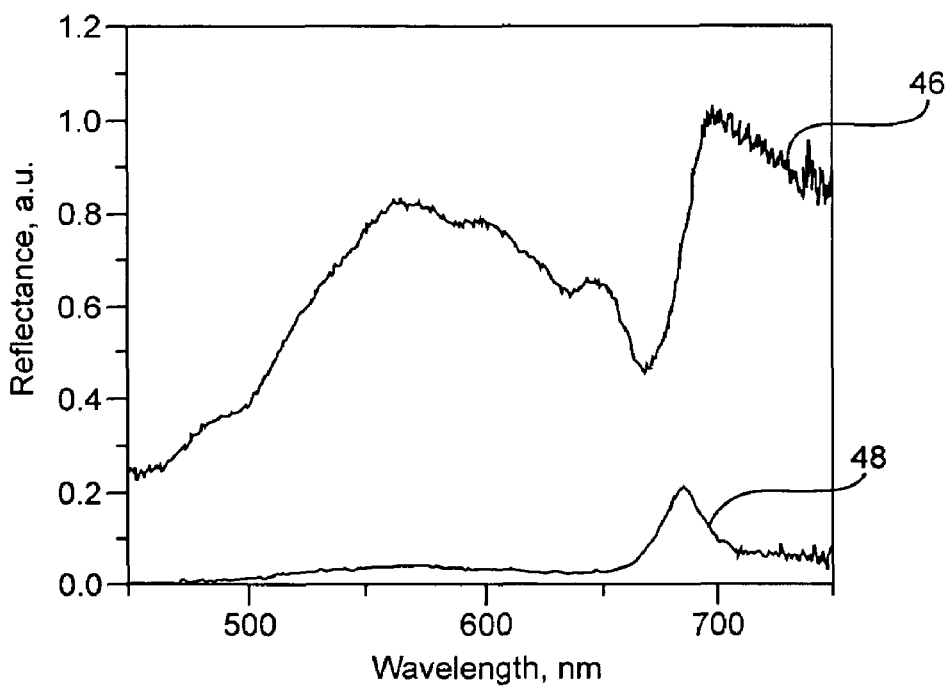
FIG. 2 is a spectral reflectance plot of maximum reflectance and minimum reflectance collected using the apparatus of FIG. 1b, corresponding to different positions of the polarizer P2.

FIG. 2 shows the detection spectra obtained by rotating the polarizer for maximum total detected light, $R_{max}(\lambda)$ 46, which consists of parallel elastic/reflection component, $R_\perp(\lambda)$, plus half the fluorescence, $0.5Fl(\lambda)$, due to the chlorophyll band (peak at 680 nm with a full width at half maximum 20 nm), and minimum total detected light $R_{min}(\lambda)$ 48 which consists of any cross-polarized elastic/reflection component, $R_\parallel(\lambda)$, plus half the fluorescence, $0.5Fl(\lambda)$, due to the chlorophyll band (peak at 680 nm with a full width at half maximum 20 nm). Now $$R_{max}(\lambda)=R_\perp(\lambda)+0.5Fl(\lambda), \quad (1)$$

$$R_{min}(\lambda)=R_\parallel(\lambda)+0.5Fl(\lambda), \quad (2)$$

where $R_\perp(\lambda)$ is the scattered light component with polarization parallel to the direction of the main polarization of the scattered light (perpendicular to the scattering plane); $R_\parallel(\lambda)$ is the scattered light component with polarization perpendicular to the direction of the main polarization of the scattered light (parallel to the scattering plane), which should be zero with this arrangement; and where Fl is the fluorescence component.

The measured spectra were normalized to the spectrum of the scattered light with the same light source and polarizers, but with the Spectralon plate instead of the object installed at 45 degrees to the incident light. It should be noted while $R_\parallel$ can be effectively expected to be zero, in fact imprecise geometric arrangements for illumination and detection as well as polarizer imperfections can result in a small background signal, which includes some scattering component.

The sum of (1) and (2)

$$R(\lambda)=R_\perp(\lambda)+R_\parallel(\lambda)+Fl(\lambda) \quad (3)$$

represents the spectrum of the total light reaching the polarizer 32 before the probe. It includes full unpolarized, polarized scattered light and fluorescence components.

Equation (2) with $R_\parallel(\lambda)=0$ gives $R_{min}(\lambda)=0.5Fl(\mu)$ or $$2R_{min}(\lambda)=Fl(\lambda) \quad (4)$$

Thus the fluorescence spectrum can be isolated using this polarization discrimination technique.

Figure 3:
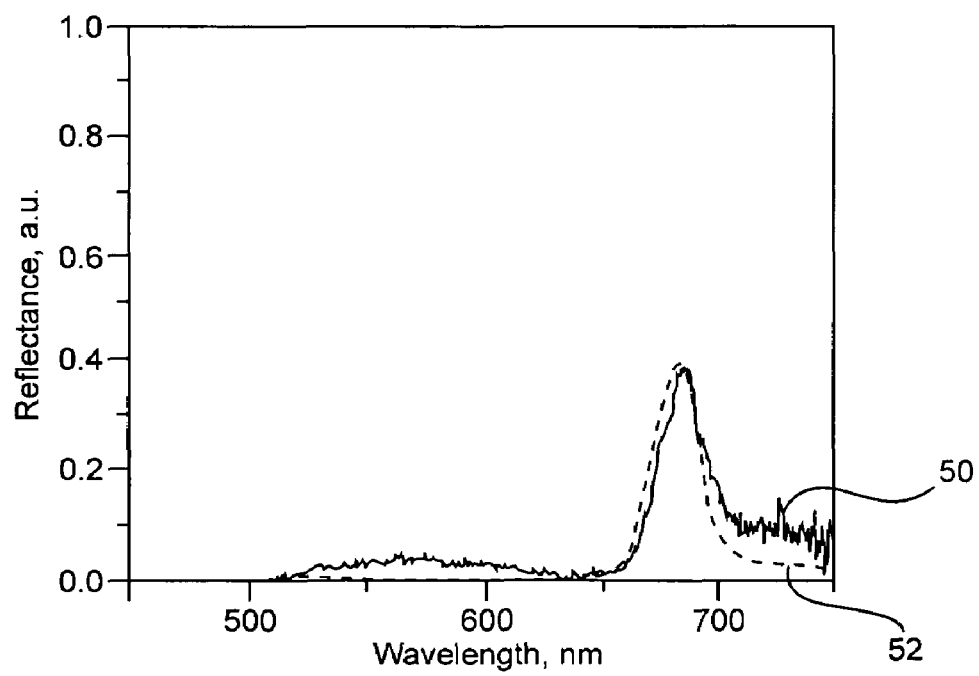
FIG. 3 is a spectral reflectance plot of the unpolarized (fluorescent) component extracted from signal collected using the apparatus of FIG. 1b.

The spectrum obtained in this manner, $2R_{min}(\lambda)$ 50, is shown in FIG. 3 with slight corrections for background subtraction. To check this result, the fluorescence of the same algae was measured using laser excitation at 488 nm. This is shown as $Fl(\lambda)_{laser}$ 52 in FIG. 3, normalized to the same peak as the $2R_{min}(\lambda)$ 50 spectrum. It is seen that the two spectra, $2R_{min}(\lambda)$ 50, and $Fl(\lambda)_{laser}$ 52 match fairly well, except where $2R_{min}(\lambda)$ 50 has a small relative shift to the red, possibly due to imperfect geometric alignments and/or multiple scattering effects. The spectrum of the elastically scattered light, $R_{s1}(\lambda)$, can then be obtained by subtracting $Fl(\lambda)_{laser}$ 52, from $R(\lambda)$, the total light reaching the polarizer P2 32 in equation (3) above.

Still more accurate derivations of the fluorescence spectra can be obtained using the polarization discrimination technique described by the following approach. The difference between (1) and (2)

$$R_s(\lambda) = R_\perp(\lambda) - R_\parallel(\lambda) \tag{5}$$

is the residual of parallel and perpendicular polarized scattered components only, and it does not contain the fluorescence component.

Figure 4:
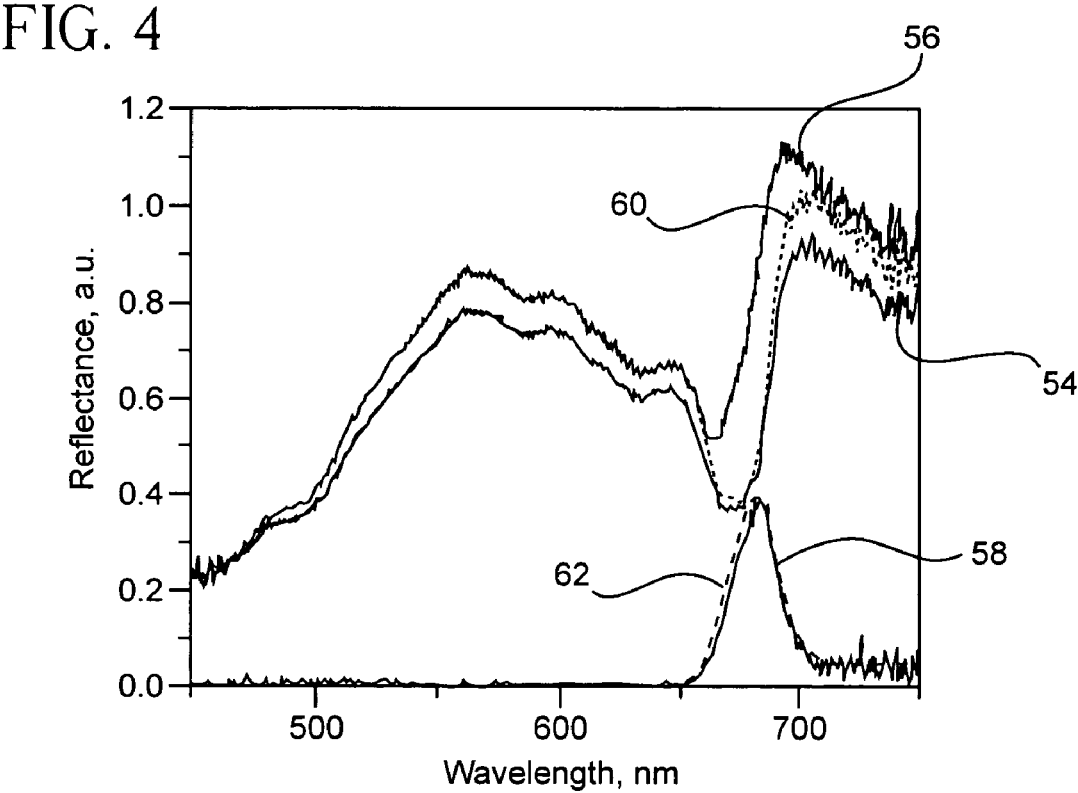
FIG. 4 is a spectral reflectance plot of parameters derived from the reflectance spectra plotted in FIG. 2, and of the extracted fluorescence. The measured laser-induced fluorescence is also plotted.

Referring to FIG. 4, since $R_\parallel(\lambda)$ is effectively zero, $R_s(\lambda)$ 54 represents the shape of the whole reflectance reaching the detector (excluding stray light effects), and should have a near-linear relationship with the total signal reaching the detector, $R(\lambda) = R_\perp(\lambda) + R_{81}(\lambda)$ 56 minus the fluorescence component $Fl(\lambda)$ 58. By fitting $R_s(\lambda)$ 54 into $R(\lambda)$ 56 outside the known fluorescence region, the fitted $R_{s1}(\lambda)$ 60 curve should then give only the elastically scattered component over the whole spectral region being considered (including the region containing fluorescence). To obtain this result, multiple regression was performed to fit the function $R_s(\lambda)$ 54 in the 450-630 nm range (outside the fluorescence region) into $R(\lambda)$ 56. The regression coefficient A and intercept B were then used to calculate the function $R_{s1}(\lambda) = A \ast R_s(\lambda) + B$ for the whole wavelength range 450-750 nm. The fluorescence $Fl(\lambda)$ component 58 in the total spectrum $R(\lambda)$ 56 can then be obtained from:

$$R(\lambda) - R_{s1}(\lambda) = Fl(\lambda). \tag{6}$$

As shown in FIG. 4, $Fl(\lambda)$ 58 obtained with this multiple regression technique is seen to be an excellent fit with the normalized $Fl(\lambda)_{laser}$ 62, demonstrating the accuracy possible with these techniques.

In another embodiment of the method and apparatus of the present invention, measurements may be taken using unpolarized light illumination. Thus, if the initial illumination in the setup of FIG. 1a is unpolarized (polarizer P1 20 is removed), the resulting equations (2), (3) and (5) would now have a significant non-zero component $R_\parallel(\lambda)$, since the illuminating light is unpolarized and now contains equal vertical as well as horizontal polarizations. Nevertheless, $R_s(\lambda)$ from (5) still represents the shape of the whole reflectance and should have close to linear relationship with the elastically reflected component of the total spectrum $R(\lambda)$ minus the fluorescence component, permitting the same curve fitting approach as used above. This was borne out by experiments.

Figure 5:
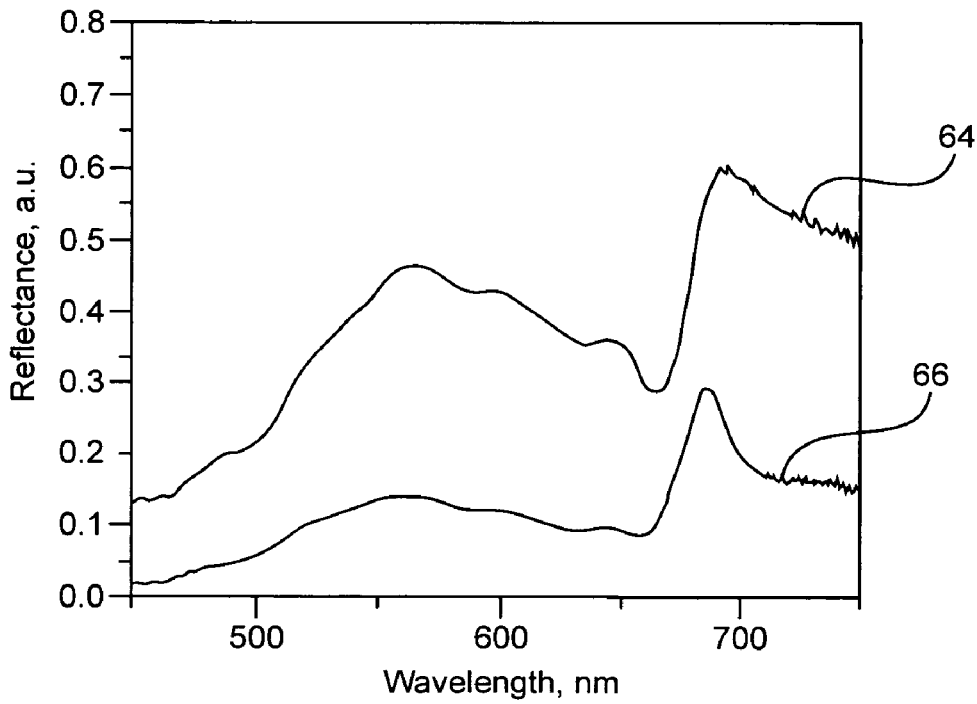
FIG. 5 is a plot of the detected maximum and minimum reflectance spectra using another embodiment of the apparatus of the present invention, which includes unpolarized illuminating light and only one polarizer, which is before the detector, to measure the reflected/scattered polarization components.
Figure 6:
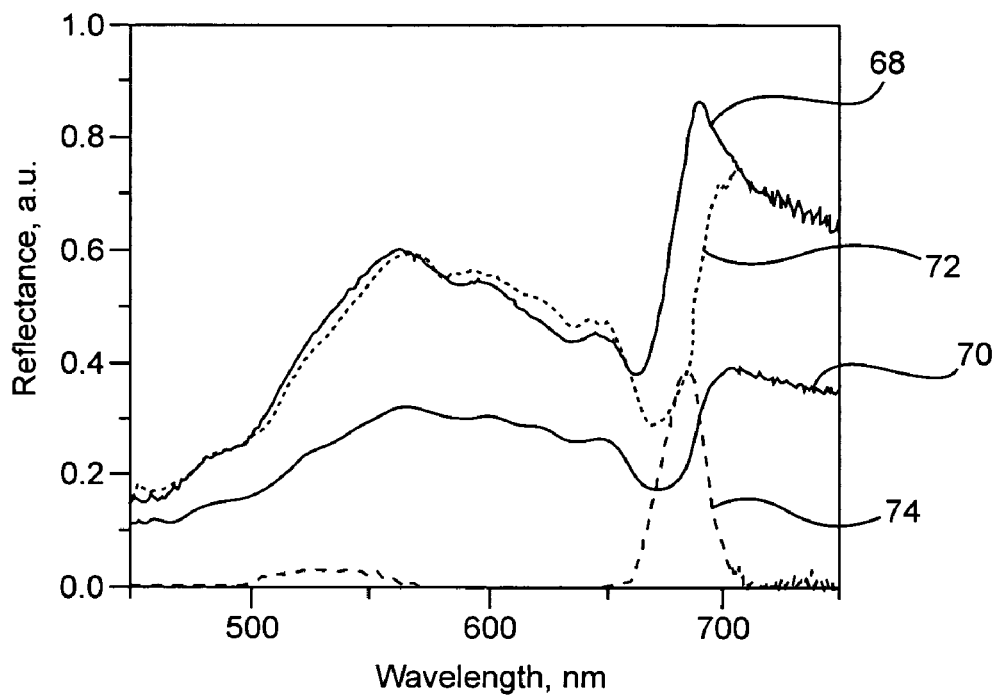
FIG. 6 is a plot of the calculated reflectance spectra for the embodiment having one polarizer.

Referring to FIG. 5, experimental results for $R_\perp(\lambda)$ 64 and $R_\parallel(\lambda)$ 66 are shown again for the same algae but without the polarizer P1 20 in FIG. 1a, i.e. with unpolarized illumination of the sample 14. The related spectra $R(\lambda)$ 68, $R_s(\lambda)$ 70, $R_{s1}(\lambda)$ 72 and $Fl(\lambda)$ 74 calculated according to the procedure described above are shown in FIG. 6. It should be noted that since the algae have dimensions large compared to visible wavelengths, making it reasonable to consider scattering from their surfaces approximately in the context of scattering from an equivalent plane, the scattering component of the vertically polarized light, $R_\parallel(\lambda)$, is much smaller than the scattering of $R_\perp(\lambda)$, the horizontally polarized light.

Figure 7:
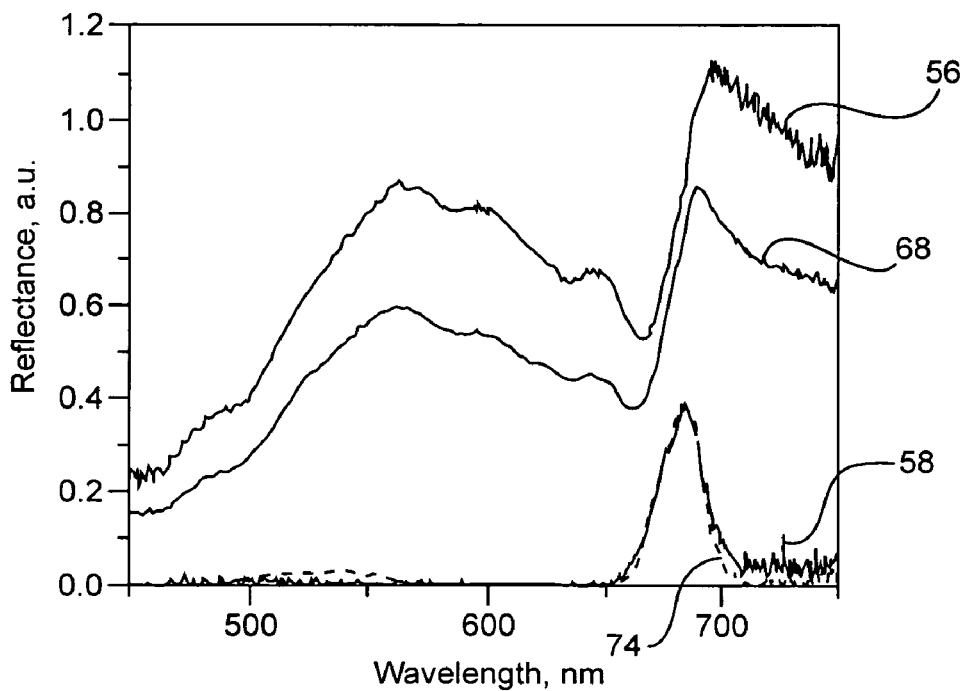
FIG. 7 is a plot of the full detected reflectance spectra and extracted fluorescence from a sample illuminated by unpolarized and horizontally polarized light.

Spectra $R(\lambda)$ and $Fl(\lambda)$ for the experiments with 1 polarizer and 2 polarizers are compared on the FIG. 7. This comparison shows that despite significant difference in the scattering by the algae illuminated by unpolarized and horizontally polarized light, the relative magnitude and spectral distribution of fluorescence calculated by the fitting technique described above is exactly the same as for the two polarizer case (described above). Furthermore, normalizing and comparing $R_{s1}(\lambda)$ obtained for the unpolarized illumination with $R_{s1}(\lambda)$ obtained for the initial horizontally polarized case shows them to have near identical dependence on wavelength.

The technique is applicable to measurements using illumination and observations subtending angles over a range where the scattered light is significantly polarized, so that the detected parallel and perpendicular components of scattered light have substantial differences between them, to permit accurate profiles of the scattering to be obtained, and a clearly defined $R_s(\lambda)$ curve obtained and used for fitting into the total spectrum $R(\lambda)$ minus the fluorescence component.

Figure 8A:
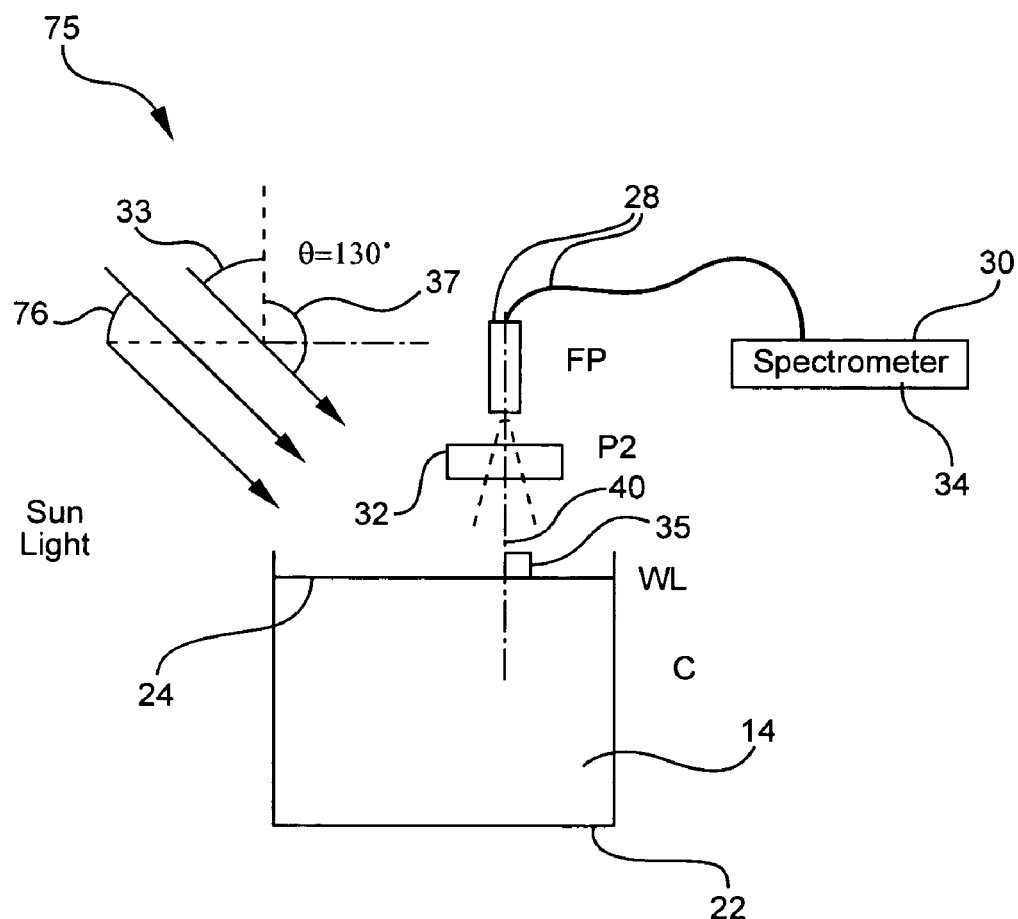
FIG. 8a is a schematic representation of an embodiment of the apparatus of the present invention, with the sunlight providing illumination of the material.
Figure 8B:
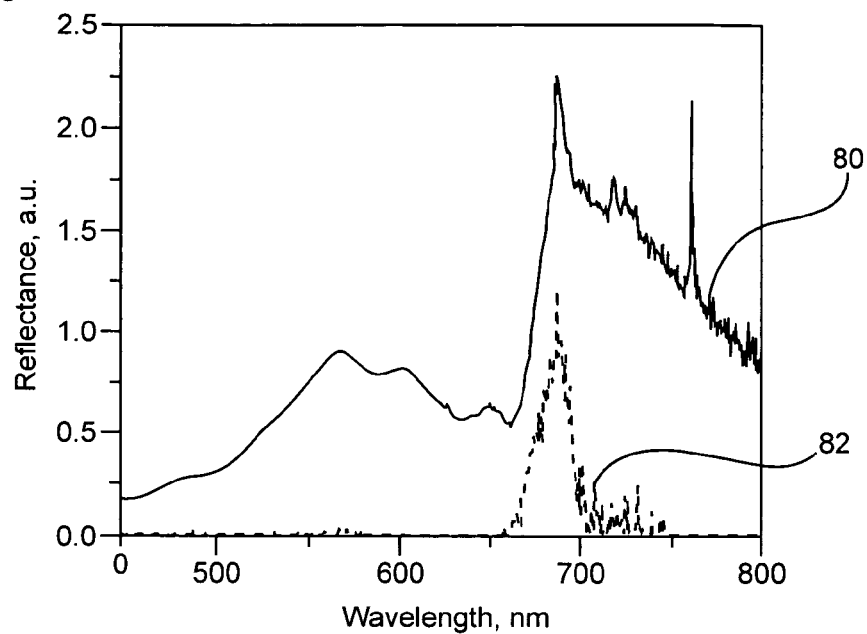

Referring to FIG. 8a, as expected, sun-induced fluorescence using the same techniques produced similar results. The measurements were conducted with an arrangement and apparatus 75 in accordance with the present invention as shown in FIG. 8a. The illumination was provided at a solar angle 76 of 40 degrees, the solar angle being defined as the angle formed between the material surface (horizontal) and the incident sunlight at the material as shown. The complementary angle to the solar angle is known as the solar zenith angle, and is defined as the angle between the normal to the surface and sun light incident on the material. The solar zenith angle, therefore, is the incident angle or illumination angle 33 of the sun. In the experimental setup 75 represented by FIG. 8a, the solar zenith or incident angle 33 was 50°. The detector probe 28 was aligned in a vertical position with the detection axis 40 normal 35 to the surface of the material 14. Consequently, the scattering angle θ 37, defined as the angle between the direction of illumination and direction of detection (detection axis), was 130°. The polarization discrimination with the larger solar angles was not sufficient enough for appropriate signal-to-noise ratio. $R(\lambda)$ 80 and fluorescence $Fl(\lambda)$ 82 obtained with solar illumination are shown in FIG. 8b. As in previous experiments, fluorescence shape was well matched with laser-induced fluorescence.

It should be noted that, in general, unpolarized light illuminating the algae will become partially (elliptically) polarized after undergoing the elastic scatter/reflection process. Some polarization will always occur for any angle of scatter, except for the forward (propagation) direction. This also holds true for larger particles such as the algae tested, where the size is large compared to the wavelength of the illuminating light, and the wavelength dependence of the scattering is dominated by the imaginary component of the refractive index (i.e. the absorption) down to individual dipole scatterers (e.g. atmospheric molecules, producing well known polarizing effects on sunlight). On the other hand, fluorescence produced by the illuminated algae will be unpolarized. This will reach the detector directly, or, in the case of higher algae concentration, after forward scattering by algae or other particulates which would still leave it unpolarized (provided the illumination and detector geometry are arranged ensure that it is only the direct fluorescence or the forward scattered fluorescence that reaches the detector).

In one embodiment, the method of the present invention includes illuminating seawater including algae, preferably with sunlight, the algae being in a concentration of up to about $4 \times 10^6$ cells/milliliter. The concentration of algae may be determined from the fluorescence spectrum extracted according to the method of the present invention.

It should be also noted that still higher accuracies in the measurement of the elastically scattered spectra can be obtained if the shape of fluorescence from the sample $Fl_0(\lambda)$ can be measured independently, for instance, by the excitation from laser light. The procedure for the retrieval of $Fl(\lambda)$ can then be more accurate. Multiple regression can be used to fit both $R_s(\lambda)$ and $Fl_0(\lambda)$ in the whole wavelength range into spectrum $R(\lambda)=A*R_s(\lambda)+B+C*Fl_0(\lambda)$ from which fluorescence spectrum is determined as $Fl(\lambda)=C*Fl_0(\lambda)$.

The degree of linear polarization of the scattered light is $p=|(P_0-P_{90})/(P_0+P_{90})|$, in our terms outside fluorescence region $p=|R_s(\lambda)/R(\lambda)|$. The value of p depends on the angle of the incident light, i.e., the incident or illumination angle, and the scattering properties of the algae. For a scattering angle 37 of 90° as in FIG. 1b, but without polarizer P1 20, p was around 0.6 at original concentration and was down to 0.25 after 64 times dilution. With P1 installed as in FIG. 1b, p was close to 0.9. For the experiments with the sun light using the apparatus of FIG. 8a, p was around 0.15. In the present invention, higher values of p mean smaller difference between the shapes of $R_s(\lambda)$ and $R(\lambda)$ and more accurate fit of the former to the latter.

In one embodiment, the method includes illuminating the material with a polarized light source at an illuminating angle from about 0° to about 90°, and orienting the detector probe normal to the sample (vertically) to collect reflected/scattered light.

In still another embodiment, the method includes illuminating the material with an unpolarized light source, for example, sunlight, at an illuminating angle from about 0° to about 45°, with the detector oriented normal to the sample.

While technique with both polarizers P1 and P2 can increase the accuracy of the measurements, it can be difficult or impossible to apply it in some cases like remote sensing applications, where the method of fluorescence retrieval using the instrument with only one polarizer is appropriate.

It should also be noted that this technique is applicable to any requirement to distinguish unpolarized light from backscattered/reflected illuminating light which is polarized to a greater or lesser degree. Thus, thermal radiation from a surface illuminated by sunlight (say) would be unpolarized. This can be relevant to a situation where thermal radiation in the 1 to 4 microns band is being viewed, e.g., for temperature estimates. For this case, the same polarization discrimination technique of the present invention can be used to separate the thermal radiation from the solar illumination.

The method of the present invention may also be useful in the field of environmental remote sensing such as from satellites or aircraft. For example, the method of the present invention may be adapted for use in remote measurements of ocean color to distinguish between unpolarized and polarized components of total reflected sunlight. The measurements may then be applied to determine chlorophyll fluorescence or fluorescence of other constituents and thereby their concentrations, or of the chlorophyll content of vegetation.

The method may also be used in the medical field for diagnostic purposes to determine the fluorescence component in the total reflection of a specimen, tissue or other bodily material, and, hence, to identify the characteristic fluorescences which are often indicators of other medical conditions, such as cancer.

Still other applications can be in the field of lidar, where it may be desired to separate fluorescence backscatter from Raman backscatter. The Raman backscatter will be polarized while the fluorescence backscatter will not be.

Also in sky observations, backscatter of illuminating sunlight will show the polarizations associated with it while fluorescence emissions in the atmosphere will be unpolarized if observed in forward scatter and so may be distinguished from the illuminating light using the above polarization technique. Furthermore, even if not observed in forward scatter, since they are unpolarized where they emit, they will have a different polarization than the scatter of the illumination causing the excitation, since the latter is already polarized at the point of absorption by the fluorescent species. These differences in polarizations may serve to distinguish fluorescence (or any other unpolarized radiation) from the exciting radiation.

The method of the present invention may also be applied to separate the fluorescence spectrum of a material from a full reflectance spectrum which includes the full reflectance spectra of both the material and additional sources of scatter.

The fluorescence spectrum of a material in the presence of additional scatterers may be extracted in accordance with the method and apparatus of the present invention. As an example, a fluorescence spectrum of algae in various clay concentrations may be extracted (see Example).

EXAMPLE

The method of the present invention was successfully applied in the laboratory to four types of algae with different particle shapes (spheres, ellipsoids, plates) and different sizes 5-18 microns (µ), and concentrations up to $4\times10^6$ cells/ml. The method was also tested with in-situ field measurements along eastern Long Island. The method of the present invention allows the extraction of fluorescence for the whole range of solar zenith angles of illumination from 0° to 90° for polarized light sources and up to 45° for unpolarized light and sunlight. In this example, the detector probe was oriented normal to the sample, i.e., vertically. In laboratory experiments, this was found to hold true even with surface waves when signal averaging of the detected signal is used. Comparison of this method for polarized and unpolarized illumination with other methods used to estimate Chlorophyll concentration showed very good correlation with the calculation of fluorescence height over baseline. The experiments performed are described below.

Figure 9:
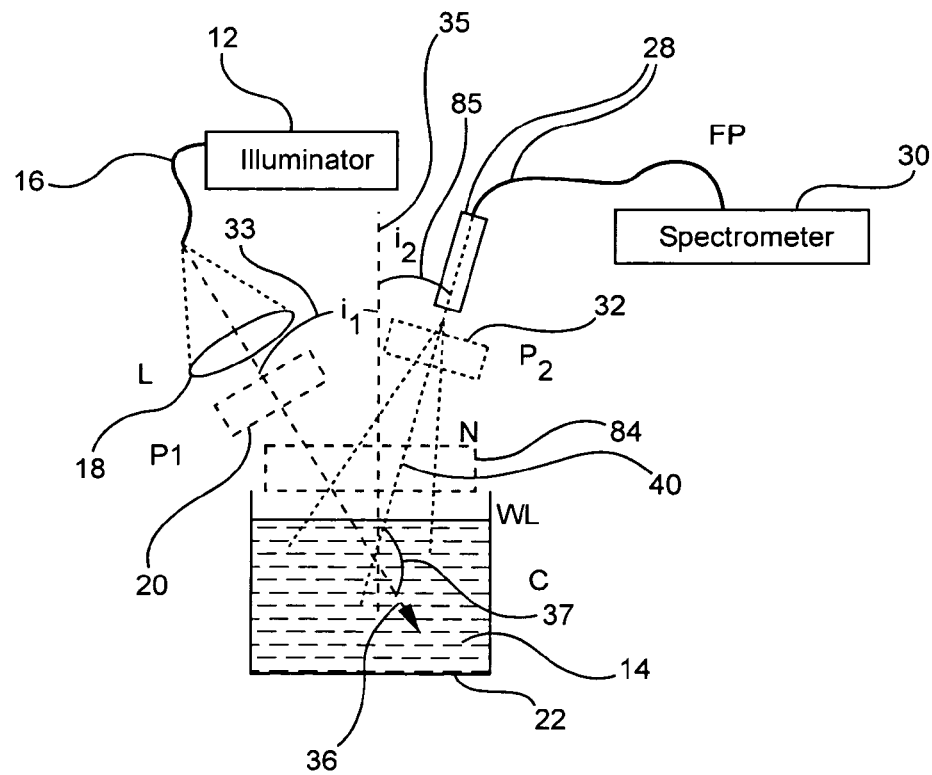
FIG. 9 is a schematic representation of another embodiment of the apparatus of the present invention, using a broadband illuminator.

Experiments were carried out with both polarized and unpolarized sources, including sunlight, both in the laboratory and in the field. The basic laboratory experimental set-up is shown in FIG. 9, which includes the same components as FIG. 1a, as indicated. The angle of illumination 33 could be varied using this setup, which also included an air nozzle 84 to induce water surface roughness. FIG. 9, therefore, represents a variety of possible alignments of the apparatus of the present invention, showing, e.g., that the detection axis 40 may be varied from the surface normal 35 to vary the detection angle 85.

Experiments were carried out with pure algae as well as with additions of different concentrations of 2 types of clay: Na-Montmorillonite and Ca-Montmorillonite. The algae *Isochrysis* sp. are largely spherical with approximately 5 microns (µm) diameter. Concentrations tested were approximately $10^6$ cells/ml. Both types of clay additives, Na-Montmorillonite and Ca-Montmorillonite, have particulates with diameters in the range 2-6 µm. The concentration of clay was varied from 10 mg/L to 1000 mg/L.

To examine the impact of additional scattering on the application of the polarization discrimination fluorescence measurement technique, clay particles were added to a constant concentration of algae in seawater. Addition of the clay particles are known to lead to both an increase of scattering/reflections as well as a change of the shape of the total scattering/reflectance spectrum. Scattering and fluorescence from the mixture was investigated using both polarized and unpolarized light sources. With clay concentrations ranging from 10 mg/L to 500 mg/L the fluorescence magnitude and shape extracted by the technique remained almost the same as with pure algae. The angle of illumination, $i_1$ 33, was about 90°. There were no significant differences in results in using the technique with either two (2) polarizers or one (1) polarizer.

Figure 10:
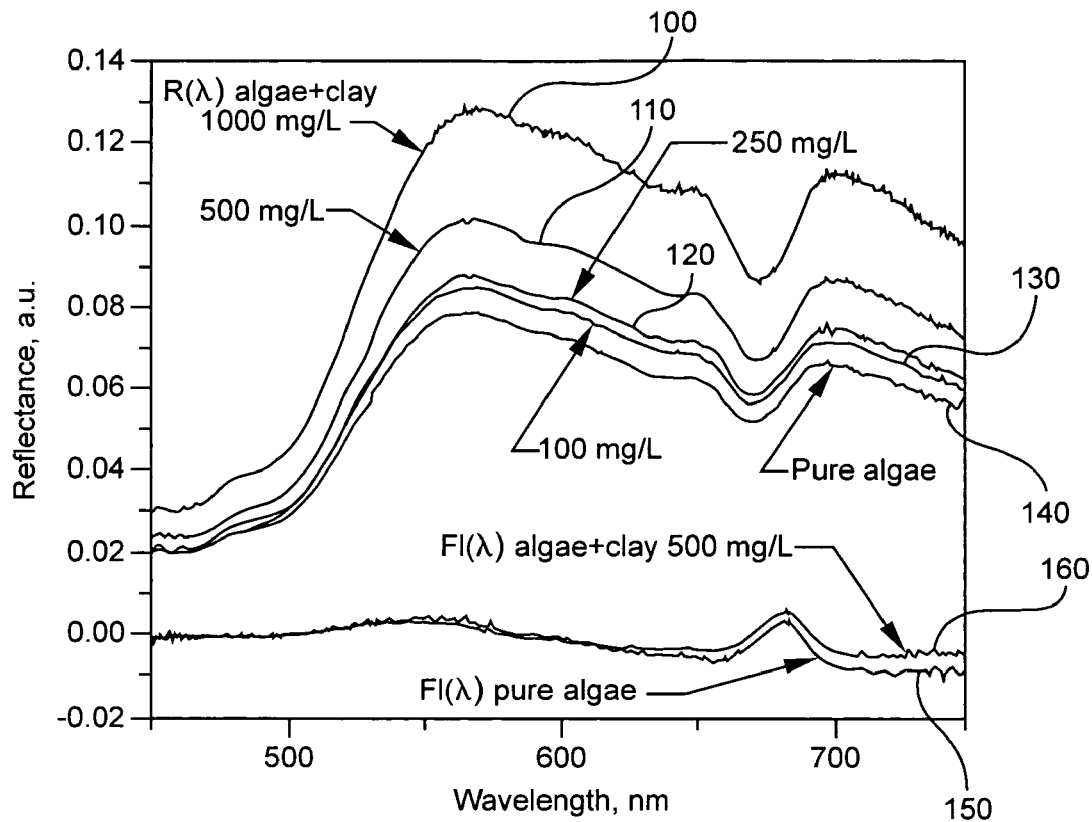
FIG. 10 is a plot of full reflectance spectra and extracted fluorescence for algae in the presence of various concentrations of clay, derived using the apparatus of FIG. 9.

FIG. 10 shows the total scatter/fluorescence signal, $R(\lambda)$, obtained for different concentrations of clay while keeping the algae concentration constant.: 1000 mg/L 100, 500 mg/L 110, 250 mg/L 120, 100 mg/L 130, and pure algae 140. Comparison of extracted fluorescence for pure algae 150 and for high concentration of clay (500 mg/L) with the algae 160 is also shown in FIG. 10. It is interesting to note that even at the high clay concentrations, in the multiple scattering regime, the extracted fluorescence was a very good match with the pure algae case, confirming applicability of the technique under these conditions.

Figure 11:
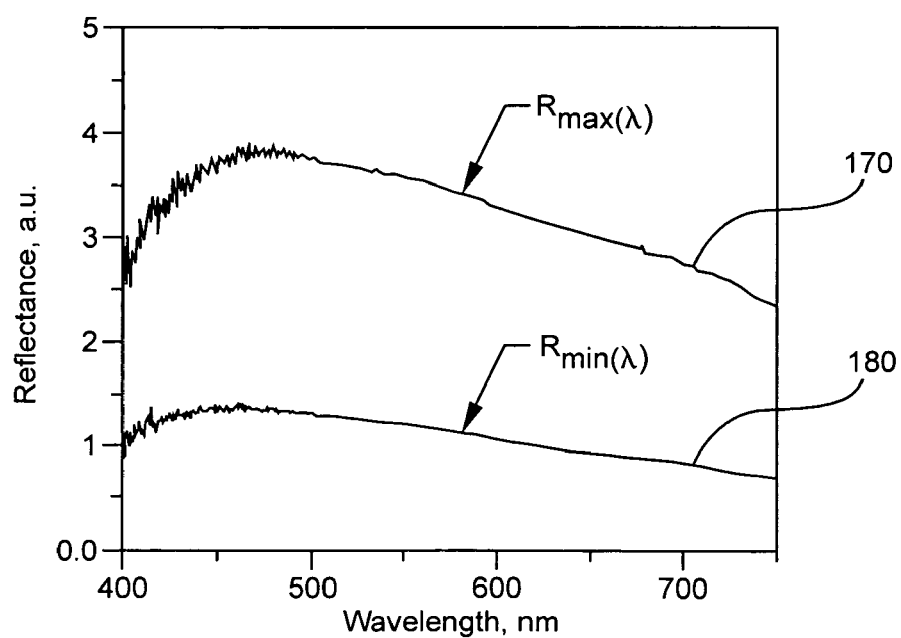
FIG. 11 is a plot of the maximum and minimum reflectance Spectra for pure clay in seawater, derived using the apparatus of FIG. 9.

To understand the range of possible applicability of this technique with different types of clays, the reflectance spectra of the pure clays in seawater for polarized and unpolarized illumination and two mutually perpendicular positions of the analyzing polarizer in front of the detector were also measured. Concentrations of clay for both types of clay Na-Montmorillonite and Ca-Montmorillonite varied from 50 mg/L to 500 mg/L. One pair of the maximum 170 and minimum 180 reflectance spectra obtained for pure clay using an unpolarized light source is shown in FIG. 11. Application of the regression procedure explained supra for these spectra showed a very good fit of $R_D(\lambda)=R_{max}(\lambda)-R_{min}(\lambda)$ into $R_s(\lambda)=R_\perp(\lambda)+R_\parallel(\lambda)$. The correlation coefficient for spectra in FIG. 11 was 0.9867. Similar numbers have been obtained for other conditions for both types of clay. This explains the successful retrieval of fluorescence presented in FIG. 10 as well as gives the possibility of the usage of the method of the present invention under different conditions, including in the presence of additional scatterers.

The results of recent experiments and analysis on the polarization discrimination technique of the present invention to separate elastic reflectance and fluorescence components resulting from white light illumination of a material was successfully applied to measurements of seawater algae of different sizes and shapes in the laboratory. It was shown that fluorescence can be effectively extracted for any angle of illumination with a polarized light source, and less accurately but still reliably with unpolarized light for at least a certain range of illumination angles. Magnitudes of the fluorescence peak extracted through polarization discrimination correlate very well with the peaks of the reflectance curves over the baseline for different concentrations of algae. The results of experiments on the impact of surface roughness on the efficacy of the technique showed that even in the presence of appreciable surface roughness the fluorescence can be accurately extracted with appropriate time averaging during the spectral acquisition process.

Fluorescence was also successfully retrieved from the algae with different concentrations of clays like Na-Montmorillonite and Ca-Montmorillonite with polarized and unpolarized light sources.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method for separating fluorescent light induced in a material by a light source from elastically scattered/reflected light in a full reflectance spectrum of the material, the light source comprising a spectrum, the method comprising:

comparing the full reflectance spectrum to a residual polarization reflectance spectrum over a nonfluorescing portion of the spectrum, the residual polarization reflectance spectrum comprising substantially no fluorescent light; and extrapolating a fluorescence spectrum, the fluorescence spectrum representing a spectral dependence of the fluorescent light over the spectrum, from the residual polarization reflectance spectrum and the full reflectance spectrum.

2. The method of claim 1, the act of comparing further comprising:

measuring a maximum polarization reflectance spectrum;

measuring a minimum polarization reflectance spectrum; and calculating the residual polarization reflectance spectrum as a difference between the maximum polarization reflectance spectrum and the minimum polarization reflectance spectrum.

3. The method of claim 1, further comprising fitting the residual polarization reflectance spectrum into the full reflectance spectrum over the nonfluorescing portion of the spectrum to derive a fitted reflectance spectrum representing substantially only the elastically scattered/reflected light over the spectrum.

4. The method of claim 3, the act of extrapolating comprising calculating the difference between the full reflectance spectrum and the fitted reflectance spectrum to extrapolate the fluorescence spectrum.

5. The method of claim 4, the method further comprising extracting a magnitude of a peak of the fluorescence spectrum, the magnitude of the peak being a measure of a characteristic of the material; and extracting a wavelength corresponding to the peak, the wavelength being another measure of a characteristic of the material.

6. The method of claim 1, wherein the light source is linearly polarized before illuminating the material.

7. The method of claim 6, wherein the light source is horizontally linearly polarized.

8. The method of claim 1, wherein the material comprises algae, the method further comprising:

extracting a magnitude of a peak of the fluorescence spectrum, the magnitude being a measure of at least one of chlorophyll concentration and photosynthetic activity.

9. The method of claim 1, wherein the light source comprises a broadband spectrum.

10. The method of claim 9, wherein the broadband spectrum is provided by sunlight.

11. The method of claim 3, the step of fitting further comprising applying multiple regression to calculate the fitted reflectance spectrum.

12. The method of claim 1, further comprising:

obtaining a laser-induced fluorescence spectrum using a laser light source; and fitting a function representing the sum of the residual polarization reflectance and the fluorescence spectra into the full reflectance spectrum over the spectrum, the fluorescence spectrum being approximated as a product of a scale factor and the laser-induced fluorescence spectrum, the act of extrapolating further comprising calculating the fluorescence spectrum from the product.

13. The method of claim 1, wherein the elastically scattered/reflected light comprises Raman backscatter, the method being adapted for use in a Raman lidar system.

14. The method of claim 1, the method being adapted for use in a sky observation system, the fluorescent light comprising fluorescence emissions in the atmosphere.

15. A method for separating fluorescent light induced in a material by a light source from elastically scattered/reflected light in a full reflectance spectrum of the material, the method comprising:
providing a linearly polarized light source;
measuring a minimum reflectance spectrum including a cross polarized component of the elastically scattered/reflected light; and
extracting a fluorescence spectrum from the minimum reflectance spectrum.

16. The method of claim 15, the act of extracting further comprising:
multiplying the minimum reflectance spectrum by a scale factor; and
correcting the scaled minimum reflectance spectrum for background.

17. The method of claim 16, wherein the scale factor is substantially equal to 2.

18. The method of claim 15, further comprising normalizing the minimum reflectance spectrum to a reflectance standard installed at 45 degrees to the light source in place of the material.

19. The method of claim 18, wherein the reflectance standard is a Spectralon plate.

20. The method of claim 15, the act of measuring further comprising rotating a linear polarizer in front of a detector until a minimum light signal is detected, a position of the linear polarizer for minimum light signal representing the cross polarized component.

21. A method for separating unpolarized light from backscattered/reflected light in a full reflectance spectrum of a surface illuminated by a light source, the light source comprising a spectrum, the method comprising:
comparing the full reflectance spectrum to a residual polarization reflectance spectrum over a portion of the spectrum comprising substantially no unpolarized light, the residual polarization reflectance spectrum comprising substantially no unpolarized light; and
extrapolating an unpolarized spectrum of the unpolarized light over the spectrum from the residual polarized reflectance spectrum and the full reflectance spectrum.

22. The method of claim 21, the act of comparing further comprising:
measuring a maximum polarization reflectance spectrum;
measuring a minimum polarization reflectance spectrum; and
calculating the residual polarization reflectance spectrum as a difference between the maximum polarization reflectance spectrum and the minimum polarization reflectance spectrum.

23. The method of claim 21, further comprising fitting the residual polarization reflectance spectrum into the full reflectance spectrum over the portion of the spectrum to derive a fitted reflectance spectrum representing substantially only the elastically scattered/reflected light over the spectrum.

24. The method of claim 23, the act of extrapolating comprising calculating the difference between the full reflectance spectrum and the fitted reflectance spectrum to extrapolate the unpolarized spectrum.

25. The method of claim 23, the act of fitting further comprising applying multiple regression to calculate the fitted reflectance spectrum.

26. The method of claim 21, wherein the light source is linearly polarized before illuminating the material.

27. The method of claim 26, wherein the light source is horizontally linearly polarized.

28. The method of claim 21, wherein the light source comprises a broadband spectrum.

29. The method of claim 28, wherein the broadband spectrum is provided by sunlight.

30. The method of claim 29, the method being adapted for separation of thermal radiation from solar illumination, wherein the unpolarized light comprises thermal radiation, and further wherein the polarized light represents backscattered/reflected solar illumination.

31. An apparatus for separating unpolarized light induced in a material by a light source from elastically scattered/reflected polarized light in a full reflectance spectrum of the material, comprising:
a detector, the detector comprising an axis of detection, a scattering angle being measured between a direction of illuminating light from the light source to the material and the axis of detection;
a spectrometer, the spectrometer and detector being used to measure at least the full reflectance spectrum; and
an analyzing polarizer, at least one of a minimum detected polarization reflectance spectrum and a residual polarization reflectance spectrum being measured by the spectrometer and detector by adjusting the analyzing polarizer, wherein
a spectrum of the unpolarized light is extrapolated from the at least one of the minimum detected polarization reflectance spectrum and the residual polarization reflectance spectrum.

32. The apparatus of claim 31, wherein the analyzing polarizer is sequentially adjusted to measure each of the minimum detected polarization reflectance spectrum and a maximum detected polarization reflectance spectrum, the residual polarization reflectance spectrum being calculated as a difference between the measured minimum and maximum detected polarization reflectance spectra.

33. The apparatus of claim 31, further comprising a linear source polarizer after the light source, the linear source polarizer providing linearly polarized illuminating light to the material.

34. The apparatus of claim 31, wherein the illuminating light is provided by a broadband source.

35. The apparatus of claim 34, wherein the illuminating light comprises sunlight.

36. The apparatus of claim 31, wherein the unpolarized light comprises fluorescent light.

37. The apparatus of claim 31, adapted for use in a Raman lidar system, the elastically scattered/reflected polarized light comprising Raman backscatter.

38. The apparatus of claim 36, adapted for use in a sky observation system, the fluorescent light comprising fluorescence emissions in the atmosphere.

39. The apparatus of claim 31, further comprising a collimator, the collimator providing collimated illuminating light to the material.

40. The apparatus of claim 31, wherein the analyzing polarizer comprises one of a rotatable linear polarizer and a polarizing prism.

41. The apparatus of claim 31, wherein the scattering angle is substantially equal to ninety degrees.

42. The apparatus of claim 31, further comprising collection optics coupled to the spectrometer, the collection optics comprising a fiber optic probe.

43. The apparatus of claim 31, being adapted for separation of thermal radiation from solar illumination, the unpolarized light comprising thermal radiation, and the elastically scattered/reflected polarized light comprising backscattered/reflected solar illumination.

44. The apparatus of claim 36, wherein the material comprises algae, a magnitude of a peak of the fluorescent spectra corresponding to at least one of chlorophyll concentration and photosynthetic activity.

45. An apparatus for separating fluorescent light from light elastically scattered/reflected from a material illuminated with a broadband illumination source comprising:
   a polarization discriminator, the polarization discriminator separating the elastically scattered/reflected light from the fluorescent light, the fluorescent light being substantially unpolarized, the elastically scattered/reflected light being substantially polarized; and
   a spectrometer, the spectrometer spectrally analyzing the fluorescent light and the elastically scattered/reflected light.

46. The apparatus of claim 45, further comprising:
   a linear polarizer, the linear polarizer polarizing the broadband illumination source.

47. A method for separating fluorescence light induced in a material by broadband light from an elastic scattering/reflection component of the broadband light, comprising:
   providing polarization discrimination to separate the fluorescence light from the elastic scattering/reflection component, the fluorescence light being substantially unpolarized and the elastic scattering/reflection component being at least partially polarized; and
   spectrally analyzing the fluorescence light and the elastic scattering/reflection component.

48. The method of claim 47, further comprising linearly polarizing the broadband light.

49. The method of claim 10, the method being adapted for use with environmental remote sensing, further comprising calculating chlorophyll fluorescence of vegetation from the fluorescence spectrum.

50. The method of claim 1, the method being adapted for use in medical diagnostics, the material comprising one of a specimen, a living tissue, and a bodily material, said method further including diagnosing a medical condition from the fluorescence spectrum.

51. The apparatus of claim 36, adapted for use in an environmental remote sensor, the spectrum of the fluorescent light being used to calculate chlorophyll fluorescence of vegetation.

52. The apparatus of claim 36, adapted for use in a medical diagnostic system, the spectrum of the fluorescent light being used to diagnose a medical condition.

* * * * *